United States Patent
Shaw et al.

(10) Patent No.: US 8,765,997 B2
(45) Date of Patent: Jul. 1, 2014

(54) PROCESS FOR PREPARING 4-BORONO-L-PHENYLALANINE

(71) Applicant: Taiwan Biotech Co., Ltd., Taoyuan Hsien (TW)

(72) Inventors: Chia-Cheng Shaw, Taoyuan Hsien (TW); Kuen-Wang Sheu, Taoyuan Hsien (TW); Shu-Fen Huang, Taoyuan Hsien (TW)

(73) Assignee: Taiwan Biotech Co., Ltd., Taoyuan Hsien (TW)

( * ) Notice: Subject to any disclaimer, the term of this patent is extended or adjusted under 35 U.S.C. 154(b) by 0 days.

(21) Appl. No.: 13/910,233

(22) Filed: Jun. 5, 2013

(65) Prior Publication Data
US 2013/0331602 A1    Dec. 12, 2013

Related U.S. Application Data

(60) Provisional application No. 61/657,069, filed on Jun. 8, 2012.

(51) Int. Cl.
*C07C 229/00* (2006.01)

(52) U.S. Cl.
USPC .......................................................... 562/445

(58) Field of Classification Search
None
See application file for complete search history.

(56) References Cited

PUBLICATIONS

Malan et al., J. Org. Chem. 1998, 63, 8019-8020.*
Skaff et al., J. Org. Chem. 2005, 70, 7353-7363.*
Database Accession No. 192003:, Uehara et al., Research and Development in Neutron Capture Therapy, Proceedings of the International Congress on Neutron Capture Therapy, 10th, Essen, Germany, Sep. 8-13, 2002, 95-98. Editor(s): Sauerwein, Wolfgang; Moss, Raymond; Wittig, Andrea. Publisher: Monduzzi Editore, Bologna, Italy.*

(Continued)

*Primary Examiner* — Karl J Puttlitz
(74) *Attorney, Agent, or Firm* — Fishman & Associates, LLC.

(57) ABSTRACT

Provided is a process for preparing 4-borono-L-phenylalanine, which has steps of: reacting N-protected (S)-4-halophenylalanine of formula (I), a boronating agent and an organolithium to obtain a reaction mixture, wherein the reaction mixture comprises N-protected (S)-4-boronophenylalanine of formula (II) and the R group represents a protecting group;

formula (I)

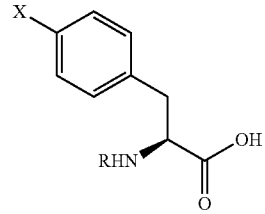

formula (II)

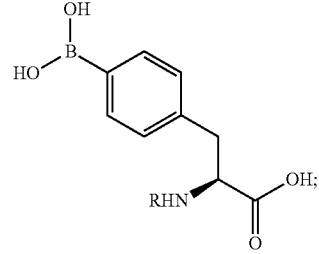

isolating the N-protected (S)-4-boronophenylalanine from the reaction mixture;
deprotecting the R group of the N-protected (S)-4-boronophenylalanine to obtain L-BPA.

20 Claims, 1 Drawing Sheet

(56) References Cited

PUBLICATIONS

Hiroyuki Nakamura et al., "A Practical Method for the Synthesis of Enantiomerically Pure 4-Borono-L-Phenylalanine", Bull. Chem. Soc. Jpn., (2000), 73, pp. 231-235. The Chemical Society of Japan.

Falk Weinhold et al., "Synthesis of Functionalized Benzoboroxoles for the Construction of Boronolectins", Synthesis, (2011), 24, pp. 4059-4067. Georg Thieme Verlag Stuttgart-New York.

extended European search report (eESR) of related EPC Application No. 13190413.8, dated Jan. 31, 2014.

* cited by examiner

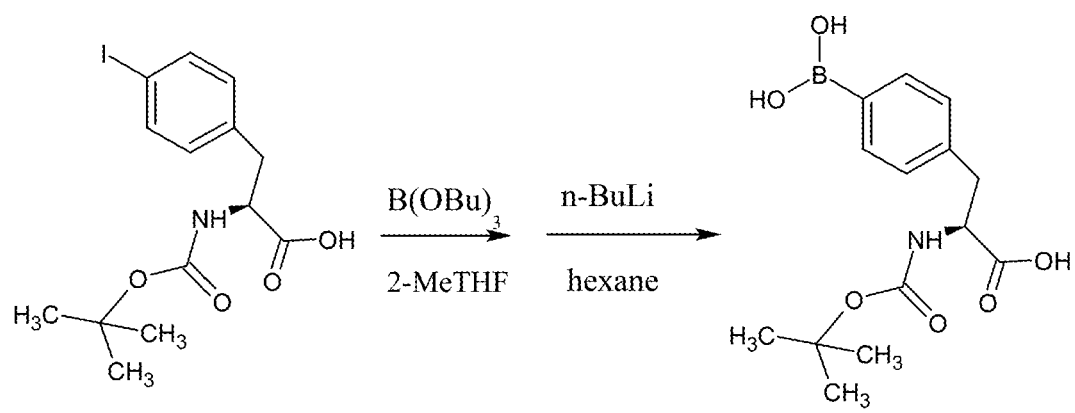

PROCESS FOR PREPARING 4-BORONO-L-PHENYLALANINE

CROSS-REFERENCE TO RELATED APPLICATION

Pursuant to 35 U.S.C. §119(e), this application claims the benefit of the priority to U.S. Provisional Patent Application No. 61/657,069, filed Jun. 8, 2012. The content of the prior application is incorporated herein by its entirety.

BACKGROUND OF THE INVENTION

1. Field of the Invention

The present invention relates to a process for preparing 4-borono-L-phenylalanine (L-BPA), particularly to a process that is timesaving, efficient, cost effective and environmentally friendly.

2. Description of the Prior Arts 4-borono-L-phenylalanine (L-BPA) is an important boronated compound known to be useful for treatment of cancer through boron neutron capture therapy (BNCT). Therefore, many syntheses of L-BPA have been developed.

As shown in formula A, two synthesis approaches of L-BPA including formation (a) and formation (b) have been developed.

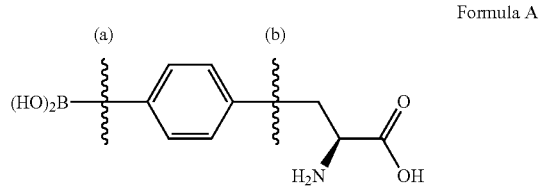

Formula A

The approach demonstrated as formation (a) is by introduction of boronic acid group into phenylalanine, which is based on forming the C—B bond directly by the introduction of the dihydroxylboryl substituent to the phenylalanine fragment. *J. Org. Chem.* 1998, 63, 8019 discloses a process undergoing palladium-catalyzed cross-coupling between an amine-protected L-4-iodophenylalanine, such as (S)—N-Boc-4-iodophenylalanine, and a diboron compound, such as bis-(pinacolato)diboron. L-BPA is then obtained after removal of the protecting group of amine and boronic acid of the phenylalanine. However, an additional pre-process is further required for preparing the boronating agent, resulting in more time consumption and complicacy of the process, and thereby failing to prepare L-BPA in high yield. The prior art discloses that the carboxylic acid of (S)—N-Boc-4-iodophenylalanine reactant is protected into benzyl ester to improve the yield of the obtained protected L-BPA up to 88%. However, an additional step of removing the benzyl ester protecting group of the carboxylic acid of the protected L-BPA is further needed, which complicates the synthetic process. Accordingly, the drawbacks of this method also include the additional pre-process for preparing the boronating agent as mentioned above, and further include the time-consuming and multi-step synthesis involving the protection step of the carboxylic acid and the deprotection step of the carboxylic acid afterwards.

Another approach demonstrated as formation (b) involving coupling reaction between an amino acid and a boron-containing benzyl or benzaldehyde fragment is also developed. *Biosci. Biotech. Biochem.* 1996, 60, 683 discloses an enantioselective synthesis of L-BPA by coupling cyclic ethers of boronic acid and a chiral derivative from L-valine, wherein the cyclic ethers of boronic acid are prepared from 4-boronobenzylbromide in advance. However, the last synthetic step of the method readily results in undesired racemization of the amino acid. Thus, an enzymatic resolution step, which typically reduces the production yield, is required to obtain optically-pure L-BPA. Accordingly, the drawbacks of this method still include the additional pre-process for preparing the boronating agent, resulting in more time consumption and complicacy of the process, and thereby failing to prepare L-BPA in high yield.

Besides, $^{10}$B contained in L-BPA is known as the critical factor accumulated in tumor cells and subsequently irradiated with thermal neutron. Thus $^{10}$B renders L-BPA a treatment of cancer through boron neutron capture therapy (BNCT). However, natural boron exists as 19.9% of $^{10}$B isotope and 80.1% of $^{11}$B isotope. Therefore, many researchers have been developing synthetic processes suitable for producing L-BPA, and preferably suitable for producing $^{10}$B-enriched L-BPA.

As disclosed in *J. Org. Chem.* 1998, 63, 8019 mentioned above, the conventional methods comprise multi-step syntheses of the boronating agents, which reduce a large amount of $^{10}$B-enriched materials during the process. As a result, the methods are not suitable for producing $^{10}$B-enriched L-BPA.

As disclosed in *Biosci. Biotech. Biochem.* 1996, 60, 683 mentioned above, an optically pure L-BPA is not obtained until the enzymatic resolution step, and also the multi-step syntheses of the boronating agent render the transformations of the $^{10}$B-enriched materials during the process. Hence, the conventional method is not suitable for producing $^{10}$B-enriched L-BPA as well.

Furthermore, *Bull. Chem. Soc. Jpn.* 2000, 73, 231 discloses a method based on coupling 4-iodo-L-phenylalanine and pinacolborane in the presence of palladium catalyst. However, since the prior art is silent on how to produce $^{10}$B-enriched L-BPA and also $^{10}$B-enriched pinacolborane is not commercially available, the method is not suitable for producing $^{10}$B-enriched L-BPA, either.

In addition, *Synlett.* 1996, 167 discloses a method by coupling iodophenylborate and L-serine zinc derivatives. The method involves indispensable pre-preparation of the L-serine zinc derivatives and the pre-preparation of the iodophenylborate, thereby giving a low yield of L-BPA. Besides, the method is still not suitable for producing $^{10}$B-enriched L-BPA, for both $^{10}$B-enriched $BI_3$ and 1,3-diphenyl-propane-1,3-diol adopted in the method are not commercially available.

To overcome the shortcomings, the present invention provides a process for preparing L-BPA to mitigate or obviate the aforementioned problems.

SUMMARY OF THE INVENTION

Given that the aforesaid drawbacks of the prior art such as large time consumption, multi-steps and additional pre-process for preparing the boronating agents, the main object of the present invention is to develop a timesaving, efficient, cost effective, and environmentally friendly process for preparing L-BPA without tedious purification. Accordingly, L-BPA prepared by the process of the present invention has high chemical purity and high optical purity.

Another main objective of the present invention is to develop a process for preparing L-$^{10}$BPA, particularly, a process for preparing L-$^{10}$BPA that is timesaving, efficient, cost effective, environmentally friendly, convenient and without tedious purification. The process in accordance with the present invention is effective in producing L-$^{10}$BPA with high chemical purity, high optical purity and high isotopic purity.

Another main objective of the present invention is to develop a process both suitable for preparing L-BPA and L-$^{10}$BPA; particularly, a process for preparing both L-BPA and L-$^{10}$BPA that is timesaving, efficient, cost effective, environmentally friendly, convenient and without tedious purification.

Accordingly, the process in accordance with the present invention comprises steps of:

reacting N-protected (S)-4-halophenylalanine of formula (I), a boronating agent and an organolithium to obtain a reaction mixture, wherein the reaction mixture comprises N-protected (S)-4-boronophenylalanine of formula (II) and the R group represents a protecting group;

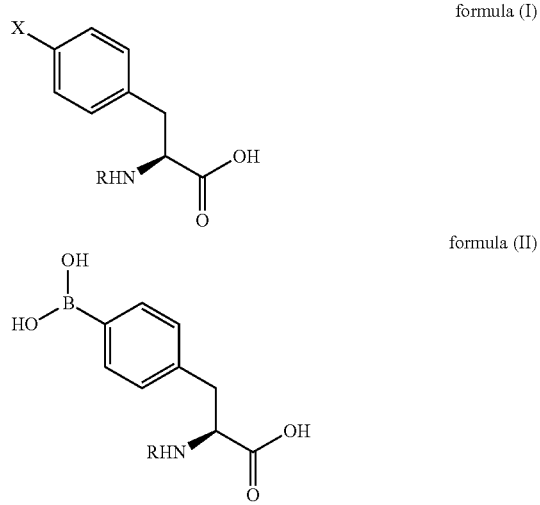

formula (I)

formula (II)

isolating the N-protected (S)-4-boronophenylalanine from the reaction mixture; and deprotecting the R group of the N-protected (S)-4-boronophenylalanine to obtain L-BPA.

According to the present invention, the boronating agent refers to any agent capable of replacing the X group of N-protected (S)-4-halophenylalanine with a boron atom through the step of reacting N-protected (S)-4-halophenylalanine of formula (I), a boronating agent and an organolithium.

According to the present invention, the boronating agent has any isotopes of boron, such as $^{11}$B, $^{10}$B or a mixture of $^{11}$B and $^{10}$B.

According to the present invention, the boronating agent having the mixture of $^{11}$B and $^{10}$B has, but not limited to, a 19.9% of $^{10}$B purity.

According to the present invention, the boronating agent includes, but is not limited to, trialkyl borate. The trialkyl borate includes, but is not limited to, tributyl borate, triethyl borate, trimethyl borate, triisopropyl borate, tripropyl borate, tri-tert-butyl borate and any other suitable trialkyl borate.

The present invention provides a process for preparing 4-borono-L-phenylalanine with several advantages. First, the present invention is a shortened process comprising a step of reacting N-protected (S)-4-halophenylalanine, a boronating agent and an organolithium to obtain N-protected (S)-4-boronophenylalanine without protecting the carboxylic acid group of N-protected (S)-4-halophenylalanine in advance, and thus deprotection of the carboxylic acid afterwards is no longer necessary. Moreover, the process in accordance with the present invention uses a boronating agent directly, and thus no additional pre-process is required for preparing the boronating agent. Also, with the simplification of process, L-BPA prepared by the process of the present invention has high chemical purity and high optical purity and an excellent overall yield. Hence, the process of the present invention is timesaving, efficient and cost effective.

Preferably, the X group of the N-protected (S)-4-halophenylalanine of formula (I) is iodide or bromide.

More preferably, the X group of the N-protected (S)-4-halophenylalanine of formula (I) is iodide.

Preferably, the R group of the N-protected (S)-4-halophenylalanine of formula (I) and of the N-protected (S)-4-boronophenylalanine of formula (II) is selected from the protecting groups which can be removed by acid consisting of: tert-butoxycarbonyl (t-Boc) group, trityl (Trt) group, 3,5-dimethoxyphenylisopropoxycarbonyl (Ddz) group, 2-(4-Biphenyl)isopropoxycarbonyl (Bpoc) group and 2-nitrophenylsulfenyl (Nps) group.

More preferably, the R group of the N-protected (S)-4-halophenylalanine of formula (I) and of the N-protected (S)-4-boronophenylalanine of formula (II) is tert-butoxycarbonyl group (t-Boc).

According to the present invention, the advantages of tert-butoxycarbonyl group are as follows.

1. N-Boc-(S)-4-halophenylalanine is solid and thereby is easily handled during the process;
2. One of the starting materials of producing N-Boc-(S)-4-halophenylalanine is Di-t-butyl dicarbonate, which is easily accessible and inexpensive, and hence the N-Boc-(S)-4-halophenylalanine thus produced is inexpensive and easily accessible as well;
3. After the tert-butoxycarbonyl group is deprotected, the tert-butoxycarbonyl group is decomposed into $CO_2$ and t-butanol, which are low hazard chemicals, and thus the present invention is safe and involves little hazard chemicals.

Preferably, the step of reacting N-protected (S)-4-halophenylalanine, a boronating agent and an organolithium to obtain a reaction mixture comprises reacting N-protected (S)-4-halophenylalanine, the boronating agent and the organolithium at a temperature ranging from −50° C. to −100° C.; and more preferably, at a temperature ranging from −70° C. to −100° C.

Preferably, the equivalent ratio of the boronating agent to the N-protected (S)-4-halophenylalanine ranges from 2 to 5. Preferably, the equivalent ratio of the organolithium to the N-protected (S)-4-halophenylalanine is at least 3. More preferably, the equivalent ratio of the organolithium to the N-protected (S)-4-halophenylalanine ranges from 3 to 10. More preferably, the equivalent ratio of the organolithium to the N-protected (S)-4-halophenylalanine ranges from 3 to 5.

Preferably, the step of reacting N-protected (S)-4-halophenylalanine, a boronating agent and an organolithium to obtain a reaction mixture includes steps of:

mixing the N-protected (S)-4-halophenylalanine, a reaction solvent and the boronating agent to obtain a mixed solution;

adding an inert organic solvent comprising the organolithium into the mixed solution, so as to obtain the reaction mixture.

According to the present invention, the concentration of the organolithium comprised in the inert organic solvent ranges from, but is not limited to, 1M to 3 M. More preferably, the concentration of the organolithium comprised in the inert organic solvent ranges from, but is not limited to, 1M to 2M.

Preferably, the step of adding an inert organic solvent comprising the organolithium into the mixed solution, so as to obtain the reaction mixture, comprises adding the inert organic solvent comprising the organolithium at a temperature ranging from −50° C. to −100° C. More preferably, at a temperature ranging from −70° C. to −100° C. More preferably, at a temperature ranging from −70° C. to −85° C.

More preferably, the step of adding an inert organic solvent comprising the organolithium into the mixed solution, so as to obtain the reaction mixture comprises adding the inert organic solvent comprising the organolithium dropwise into the mixed solution due to the vigorous reaction of the mixed solution and the organolithium. The time of adding the inert organic solvent comprising the organolithium dropwise into the mixed solution depends on, but not limited to, the amount of the inert organic solvent comprising the organolithium, the concentration of the organolithium comprised in the inert organic solvent, and the amount of the mixed solution; for example, when the volume of the mixed solution ranges from 300 mL to 400 mL and the volume of the inert organic solvent comprising the organolithium ranges from 50 mL to 100 mL, the time of adding the organolithium in the inert organic solvent dropwise to the mixed solution is within 2 to 3 hours.

Since the reaction of the mixed solution and the organolithium is vigorous, the step of mixing the N-protected (S)-4-halophenylalanine, a reaction solvent and the boronating agent to obtain a mixed solution comprises mixing the N-protected (S)-4-halophenylalanine, a reaction solvent and the boronating agent under nitrogen to obtain a mixed solution and the step of adding the inert organic solvent comprising the organolithium solvent into the mixed solution comprises adding the inert organic solvent comprising the organolithium solvent into the mixed solution under nitrogen, so as to obtain the reaction mixture.

Preferably, the step of isolating the N-protected (S)-4-boronophenylalanine from the reaction mixture includes steps of:

adding an aqueous solution to the reaction mixture to obtain a first aqueous layer, extracting the first aqueous layer with an extractive solvent to obtain a second aqueous layer;

adjusting the pH value of the second aqueous layer to less than 4 to crystallize the N-protected (S)-4-boronophenylalanine;

filtering the crystals of the N-protected (S)-4-boronophenylalanine and then drying the crystals of the N-protected (S)-4-boronophenylalanine, so as to obtain the N-protected (S)-4-boronophenylalanine from the second aqueous layer.

The step of adjusting the pH value of the second aqueous layer to less than 4 to crystallize the N-protected (S)-4-boronophenylalanine includes a step of adjusting the pH value of the second aqueous layer to less than 4 by adding an acidic solution into the second aqueous layer to crystallize the N-protected (S)-4-boronophenylalanine, and more preferably, to adjust the pH of the second aqueous layer to range from 3 to 4.

Accordingly, the step of isolating the N-protected (S)-4-boronophenylalanine from the reaction mixture of the present invention is simplified and without any tedious purification, thereby successfully obtaining pure N-protected (S)-4-boronophenylalanine. Therefore, the present invention provides a simplified process without tedious purification, thereby avoiding a waste of solvent and silica gel. Thus, the present invention is environmentally friendly.

Preferably, the step of deprotecting the R group of the N-protected (S)-4-boronophenylalanine to obtain L-BPA includes steps of acidifying a first organic solvent comprising the N-protected (S)-4-boronophenylalanine to deprotect the R group of N-protected (S)-4-boronophenylalanine, so as to obtain L-BPA.

According to the present invention, the step of acidifying a first organic solvent comprising the N-protected (S)-4-boronophenylalanine to deprotect the R group of N-protected (S)-4-boronophenylalanine includes steps of acidifying a first organic solvent comprising the N-protected (S)-4-boronophenylalanine by adding an acidifying solution to deprotect the R group of N-protected (S)-4-boronophenylalanine, so as to obtain L-BPA.

According to the present invention, the step of acidifying a first organic solvent comprising the N-protected (S)-4-boronophenylalanine to deprotect the R group of the N-protected (S)-4-boronophenylalanine to obtain L-BPA includes steps of acidifying a first organic solvent comprising the N-protected (S)-4-boronophenylalanine to a pH lower than 3, more preferably, to a pH lower than 1, to deprotect the R group of the N-protected (S)-4-boronophenylalanine, so as to obtain L-BPA.

Preferably, the step of deprotecting the R group of the N-protected (S)-4-boronophenylalanine to obtain L-BPA includes steps of acidifying a first organic solvent comprising the N-protected (S)-4-boronophenylalanine to deprotect the R group of the N-protected (S)-4-boronophenylalanine to obtain an acidic mixture; adjusting the pH of the acidic mixture above 1 to crystallize L-BPA; and filtering the crystals of L-BPA and then drying the crystals of L-BPA, so as to obtain L-BPA from the acidic mixture.

More preferably, adjusting the pH of the acidic mixture above 1 to crystallize L-BPA includes adjusting the pH of the acidic mixture within a range from pH 1 to 3; and continuously increasing the pH of the acidic mixture till within a range from pH 5 to 7.4 to crystallize L-BPA.

More preferably, adjusting the pH of the acidic mixture above 1 to crystallize L-BPA includes adjusting the pH of the acidic mixture within a range from pH 1 to 3; allowing the acidic mixture to stand for a period of time; and continuously increasing the pH of the acidic mixture till within a range from pH 5 to 7.4 to crystallize L-BPA.

More preferably, adjusting the pH of the acidic mixture above 1 to crystallize L-BPA includes adjusting the pH of the acidic mixture within a range from pH 1.5; allowing the acidic mixture to stand for a period of time; and continuously increasing the pH of the acidic mixture till to pH 6.2 to crystallize L-BPA.

According to the present invention, the period of time includes, but is not limited to 0.5 hour and 1 hour, which is for growing more solids of L-BPA.

Accordingly, the step of deprotecting the R group of the N-protected (S)-4-boronophenylalanine to obtain L-BPA is simplified and without tedious purification, and the obtained L-BPA is with high chemical purity and high optical purity. Therefore, the present invention provides a simplified process without tedious purification, thereby avoiding a waste of solvent and silica gel. Thus, the present invention is environmentally friendly.

Preferably, the boronating agent has a $^{10}B$ purity not less than 98%.

Preferably, the 4-borono-L-phenylalanine is 4-($^{10}B$)borono-L-phenylalanine.

Preferably, the N-protected (S)-4-boronophenylalanine of formula (II) is N-protected(S)-4-($^{10}B$)boronophenylalanine.

According to the present invention, the boronating agent includes trialkyl $^{10}B$ borate and any other suitable agent containing a 99% of $^{10}B$ purity. Trialkyl $^{10}B$ borate includes, but is not limited to $^{10}B(OBu)_3$ and $^{10}B(OMe)_3$. More preferably, the $^{10}B$ boronating agent is commercially available.

The process according to the present invention is also suitable for preparing 4-($^{10}B$)borono-L-phenylalanine without additional pre-process for preparing the boronating agent. Besides, the present invention provides 4-($^{10}B$)borono-L-phenylalanine with high chemical purity, with high optical purity, with high isotopic purity and an excellent overall yield due to the shortened and simplified process, and the present invention has the same advantages of being timesaving, efficient, cost effective, without tedious purification, and environmental friendly as mentioned above.

According to the present invention, the reaction solvent includes, but is not limited to, ether-type solvent and any other suitable organic solvent. The ether-type solvent applicable in the present invention includes, but is not limited to, tetrahydrofuran, 2-methyltetrahydrofuran, ethyl ether, and any other suitable ether-type solvent. More preferably, the reaction solvent is an ether-type solvent. More preferably, the reaction solvent is tetrahydrofuran or 2-methyltetrahydrofuran.

According to the present invention, the organolithium includes, but is not limited to, n-butyl lithium, tert-butyl lithium, sec-butyl lithium, methyl lithium, phenyl lithium, and any other suitable organolithium.

According to the present invention, the inert organic solvent refers to organic material in which the organolithium is at least partially soluble and which is chemically inert to the organolithium, the N-protected (S)-4-halophenylalanine of formula (I), and the boronating agent. The inert organic solvent includes, but is not limited to, alkanes, ether-type solvents and any other suitable organic solvent. The alkanes include, but are not limited to, hexanes, heptane, cyclohexane, pentane, and any other suitable alkanes. The ether-type solvents include, but are not limited to, tetrahydrofuran, diethyl ether, diethoxymethane, dibutyl ether, 2-methyltetrahydrofuran and any other suitable ether-type solvents.

According to the present invention, the extractive solvent refers to any solvent substantially immiscible with water or slightly immiscible with water.

The extractive solvent includes, but is not limited to, isobutyl alcohol, toluene, n-butyl alcohol, isopropyl acetate, ethyl acetate, and any other suitable extractive solvent.

According to the present invention, the acidic solution includes, but is not limited to, hydrochloric acid solution and any other suitable acidic solution.

According to the present invention, the first organic solvent includes, but is not limited to, acetone, tetrahydrofuran, dioxane, and any other suitable organic solvent. More preferably, the first organic solvent is acetone.

According to the present invention, the acidifying solution includes, but is not limited to, hydrochloric acid in dichloromethane, trifluoroacetic acid in dichloromethane, methanesulfonic acid in dioxane, trimethylsilyl chloride in dichloromethane. More preferably, the acidifying solution is a solution comprising hydrochloric acid.

Other objectives, advantages and novel features of the invention will become more apparent from the following detailed description when taken in conjunction with the accompanying drawings.

BRIEF DESCRIPTION OF THE DRAWINGS

FIG. 1 is a chemical equation illustrating an embodiment of the invention.

DETAILED DESCRIPTION OF THE PREFERRED EMBODIMENTS

The present invention provides solutions to solve the problems of the conventional processes for preparing L-BPA. A process for preparing L-BPA from (S)—N-Boc-4-iodophenylalanine is provided as a preferred embodiment of (S)—N-Boc-4-halophenylalanine for illustrating but not limiting the scope of the present invention.

For a better understanding about the technical features of the present invention and its effect, and for implements in accordance with the disclosures of the specification, preferred embodiment, details and figures are further shown as follows.

The materials and conditions involved in the embodiments of the present invention are:

(S)—N-Boc-4-iodophenylalanine, with a purity not less than 96.8%.

The reaction solvent: 2-methyltetrahydrofuran.

The boronating agent: tributyl borate or $^{10}B$ tributyl borate.

The organolithium is n-butyllithium.

The inert organic solvent is hexanes.

The concentration of the organolithium comprised in hexanes is 1.6 M.

The extractive solvent is isobutyl alcohol.

The acidic solution is hydrochloric acid.

The equivalent ratio of the boronating agent to (S)—N-Boc-4-halophenylalanine is 3.5.

The equivalent ratio of the organolithium to (S)—N-Boc-4-halophenylalanine is 4.25.

The first organic solvent is acetone.

The acidifying solution is a solution comprising hydrochloric acid.

The present invention is environmentally friendly and reduces cost remarkably since 2-methyltetrahydrofuran, isobutyl alcohol and acetone are non-toxic and are environmentally friendly solvent and since 2-methyltetrahydrofuran can be recycled after use.

Embodiment 1

Preparation of (S)—N-Boc-4-boronophenylalanine from (S)—N-Boc-4-iodophenylalanine With reference to FIG. 1, a 1-L, three-necked flask equipped with a mechanical stirrer, a thermometer, and a nitrogen inlet adaptor capped with a rubber septum was charged with 2-methyltetrahydrofuran (150 mL), and followed by (S)—N-Boc-4-iodophenylalanine (10.0 g, 96.8%, 24.7 mmol), stirred to form a solution, and added tributyl borate (21 mL, 17.9 g, 77.8 mmol) to form a mixed solution. The mixed solution was cooled to a temperature ranging from −76° C. to −85° C., and n-butyllithium (1.6 M in hexanes, 68 mL, 109 mmol) was added dropwise to the mixed solution over 2.5 h to form a reaction mixture. After the addition, a quenched sample of the reaction mixture was analyzed by HPLC and the starting (S)—N-Boc-4-iodophenylalanine was found less than 0.5%. The reaction mixture was quenched slowly with 180 mL of cold water over a 30 min period, then allowed to warm to a temperature ranging from 5° C. to 10° C. The resulted mixture was stirred for 10 to 20 minutes, and then was filtered to remove the insoluble material, washed with 20 mL of water, combined the water wash to the filtrate and transferred to a separatory funnel. The basic lower aqueous layer was separated to obtain a first aqueous layer. The first aqueous layer was extracted with isobutyl alcohol, and was separated from the isobutyl alcohol to obtain a second aqueous layer. The temperature of the second aqueous layer was adjusted to 20° C. to 25° C., and the pH of the second aqueous layer was adjusted to 3 to 4 by using 37% of hydrochloric acid. The product (S)—N-Boc-4-boronophenylalanine started to precipitate during this period. The second aqueous layer mixture was stirred for 30 min, the pH of the second aqueous layer mixture was readjusted to 3.0 and the second aqueous layer mixture was stirred for another 2 hours at a temperature ranging from 20 to 25° C. The second aqueous layer mixture was filtered to obtain solid (S)—N-Boc-4-boronophenylalanine, which was washed twice with 20 mL of water and dried in a vacuum oven at 50° C. for a minimum of 5 hours to a loss on drying (LOD) of less than 0.5% to afford 5.1 g of (S)—N-Boc-4-boronophenylalanine as white solid, which was 98.8% pure determined by HPLC. The yield was 66%.

The melting point, specific rotation, $^1$H NMR data, $^{13}$C NMR data, IR data and MS data of the obtained (S)—N-Boc-4-boronophenylalanine are as follows.

Melting point: 150° C. (decomp.), determined by Electrothermal 9100;

$[\alpha]_D^{25}$:+13.5° (c=0.5, MeOH);

$^1$H NMR (500 MHz, DMSO-$d_6$) δ 8.0 (singlet (s), 2H), 7.7 (doublet (d), J=7.8 Hz, 2H), 7.2 (d, J=7.8 Hz, 2H), 7.0 (d, J=8.4 Hz, 2H), 4.1 (multiplet (m), 1H), 3.0 (doublet of doublets (dd), J=13.8, 4.5 Hz, 1H), 2.8 (dd, J=13.7, 10.3 Hz, 1H), 1.3 (s, 9H);

$^{13}$C NMR (125 MHz, DMSO-$d_6$) δ 173.63, 155.48, 139.96, 134.06, 131.96, 128.18, 78.13, 55.06, 36.53, 28.19;

IR(KBr) $v_{max}$: 3328, 2979, 1716, 1689, 1537, 1370, 1345, 1332, 1285, 1165, 1040 $cm^{-1}$; and ESI (+)-MS m/z=332.0 (M+Na)$^+$.

Preparation of 4-borono-L-phenylalanine (L-BPA) from (S)—N-Boc-4-boronophenylalanine A suspension of (S)—N-Boc-4-boronophenylalanine (5.63 g, 98.5% pure, 17.9 mmol) in a mixture of acetone (34 ml) and water (3.8 ml) was stirred and added hydrochloric acid (37%, 3.8 ml) to form an acidic mixture, and the acidic mixture was stirred at 55° C. for 1.5 h. HPLC analysis of the acidic mixture showed the completion of the reaction. The acidic mixture was cooled to room temperature, and the pH of the acidic mixture was adjusted to 1.5 by using sodium hydroxide aqueous solution. The acidic mixture was stirred for 30 min, and the product 4-borono-L-phenylalanine started to precipitate during this period. The pH of the acidic mixture was readjusted to 6.2 by using sodium hydroxide aqueous solution, and the acidic mixture was stirred overnight at room temperature. The acidic mixture was filtered to obtain solid 4-borono-L-phenylalanine. The solid 4-borono-L-phenylalanine was washed with water, then with 50% aqueous acetone, and dried in a vacuum oven at 80° C. for a minimum of 6 hours to constant weight to afford 3.51 g (93.2% yield) of 4-borono-L-phenylalanine with 99.6% pure as white crystals. The obtained 4-borono-L-phenylalanine was analyzed by chiral HPLC, indicating the ratio of L to D isomers to be 100 to 0 (100% enantiometric excess).

The melting point, specific rotation, $^1$H NMR data, $^{13}$C NMR data, IR data and MS data of the obtained L-BPA are as follows.

Melting point: 275 to 280° C. (decomp.);

$[\alpha]_D^{25}$:-4.7° (c=0.5, 1M HCl);

$^1$H NMR (500 MHz, $D_2O$, $CF_3COOD$): δ 7.2 (d, J=7.9 Hz, 2H), 6.8 (d, J=8.0 Hz, 2H), 3.9 (dd, J=7.8, 5.7 Hz, 1H), 2.9 (dd, J=14.6, 5.6 Hz, 1H), 2.7 (dd, J=14.6, 7.9 Hz, 1H);

$^{13}$C NMR (125 MHz, $D_2O$, $CF_3COOD$): δ 171.81, 137.31, 135.16, 132.42, 129.65, 54.64, 36.32;

IR(KBr) $v_{max}$: 3585, 3148, 3039, 2914, 1636, 1610, 1505, 1411, 1388, 1344, 1080, 714 $cm^{-1}$; and LC-ESI (+)-MS (M+Na)$^+$=m/z 232.0.

Embodiment 2

Preparation of (S)—N-Boc-4-($^{10}$B) boronophenylalanine from (S)—N-Boc-4-iodophenylalanine Set up a 3-L, three-necked flask equipped with a mechanical stirrer, a thermometer, and a nitrogen inlet adaptor capped with a rubber septum. Charged the flask with 2-methyltetrahydrofuran (750 mL), followed by (S)—N-Boc-4-iodophenylalanine (50.0 g, 100% pure, 128 mmol), stirred to form a solution, and added tributyl $^{10}$B borate (106 mL, 90.1 g, 393 mmol) to form a mixed solution. The mixed solution was cooled to a temperature ranging from −76° C. to −85° C., and n-butyllithium (1.6 M in hexanes, 375 ml, 600 mmol) was added dropwise to the mixed solution over 3 h to form a reaction mixture.

After the addition, the reaction mixture was stirred for an additional 0.5 h at −80° C. HPLC analysis of a quenched sample of the reaction mixture showed the starting material (S)—N-Boc-4-iodophenylalanine was less than 0.5%. The reaction mixture was quenched slowly with 900 mL of cold water over 15 to 20 minutes, then allowed to warm to a temperature ranging from 5° C. to 10° C. The resulted mixture was filtered to remove insoluble solid, and 100 mL of water was adopted for transfer and rinse. The obtained filtrate was transferred to a separatory funnel to separate the layers, the basic lower aqueous layer was separated to obtain a first aqueous layer. The first aqueous layer was extracted with isobutyl alcohol and then separated from the isobutyl alcohol to obtain a second aqueous layer.

The pH of the second aqueous layer was adjusted to 3 to 4 by using 37% hydrochloric acid at a temperature ranging from 20° C. to 25° C., the product (S)—N-Boc-4-($^{10}$B) boronophenylalanine started to precipitate during this period. The second aqueous layer mixture was stirred for 30 minutes, then the pH of the second aqueous layer mixture was further adjusted to 3.0 and then the second aqueous layer mixture was stirred for another 2 hours. The second aqueous layer mixture was filtered to obtain solid (S)—N-Boc-4-($^{10}$B) boronophenylalanine, which was then washed twice with water and dried in a vacuum oven at 50° C. for a minimum of 4 hours to an LOD of less than 0.5% to afford 25.8 g of (S)—N-Boc-4-($^{10}$B) boronophenylalanine as white solid, which was 99.6% pure determined by HPLC. The yield was 65.1%.

The melting point, specific rotation, $^1$H NMR data, $^{13}$C NMR data, IR data and MS data of the obtained (S)—N-Boc-4-($^{10}$B) boronophenylalanine are as follows.

Melting point: 150° C. (decomp.);

$[\alpha]_D^{25}$:+14° (c=0.5, MeOH);

$^1$H NMR: (500 MHz, DMSO-$d_6$): δ 8.0 (s, 2H), 7.7 (d, J=7.7 Hz, 2H), 7.2 (d, J=7.6 Hz, 2H), 7.0 (d, J=8.4 Hz, 2H), 4.1 (m, 1H), 3.0 (dd, J=13.8, 4.5 Hz, 1H), 2.8 (dd, J=13.7, 10.3 Hz, 1H), 1.3 (s, 9H);

$^{13}$C NMR (125 MHz, DMSO-$d_6$) δ 173.63, 155.48, 139.96, 134.06, 131.94, 128.18, 78.13, 55.06, 36.53, 28.19;

IR (KBr) $v_{max}$: 3331, 2979, 1717, 1689, 1537, 1399, 1372, 1365, 1285, 1165, 1045 $cm^{-1}$; and HRMS (ESI): calculated for $C_{14}H_{20}^{10}BNO_6$ [M−H]$^-$ 307.1420. found 307.1333.

Preparation of 4-($^{10}$B)borono-L-phenylalanine (L-($^{10}$B) BPA) from (S)—N-Boc-4-($^{10}$B)boronophenylalanine A suspension of (S)—N-Boc-4-($^{10}$B) boronophenylalanine (20.5 g, 99.6% pure, 66.2 mmol) in a mixture of acetone (122 ml) and water (14 ml) was stirred at room temperature and added hydrochloric acid (37%, 14 ml) to form an acidic mixture, the acidic mixture was stirred at 55° C. for 1.5 to 2 hours. HPLC analysis of the acidic mixture showed the completion of the reaction. The temperature of the acidic mixture was cooled to room temperature, and the pH of the acidic mixture was adjusted to 1.5 by using sodium hydroxide aqueous solution, 4-($^{10}$B)borono-L-phenylalanine started to precipitate during this period, and the acidic mixture was stirred for 50 min. The pH of the acidic mixture was readjusted to 6.2 by using sodium hydroxide aqueous solution, and the mixture was stirred for a minimum of 25 minutes at room temperature. The acidic mixture was filtered to obtain solid 4-($^{10}$B)borono-L-phenylalanine. The solid 4-($^{10}$B)borono-L-phenylalanine was washed with 50% aqueous acetone, followed by an acetone rinse, dried in a vacuum oven at 80° C. for a minimum of 6 hours to constant weight to afford 13.3 g (96.4% yield) of 4-($^{10}$B)borono-L-phenylalanine with 99.9% pure as white crystals, and was analyzed by chiral HPLC, indicating the ratio of L to D isomers to be 100 to 0 (100% enantiometric excess).

The melting point, specific rotation, $^1$H NMR data, $^{13}$C NMR data, IR data, ICP-MS data and HRMS data of the obtained L-($^{10}$B) BPA are as follows.

Melting point: 275 to 280° C. (decomp.);
$[\alpha]_D^{25}$: −5.4° (c=0.5, 1M HCl);
$^1$H NMR (500 MHz, D$_2$O, CF$_3$COOD): δ 7.2 (d, J=8.0 Hz, 2H), 6.8 (d, J=8.0 Hz, 2H), 3.9 (dd, J=7.8, 5.7 Hz, 1H), 2.8 (dd, J=14.6, 5.6 Hz, 1H), 2.7 (dd, J=14.6, 7.9 Hz, 1H);
$^{13}$C NMR: (125 MHz, D$_2$O, CF$_3$COOD): δ 171.80, 137.31, 135.16, 132.37, 129.65, 54.64, 36.32;
IR(KBr) v$_{max}$: 3585, 3148, 3038, 2923, 1636, 1610, 1507, 1410, 1398, 1345, 1085, 716 cm$^{-1}$.
ICP-MS measurements for $^{10}$B content is higher than 99.4 (w/w %), wherein $^{10}$B is compared to $^{11}$B; and
HRMS (ESI): calculated for C$_9$H$_{13}$10BNO$_4$, [M+H]$^+$ 209.0974. found 209.0970.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A process for preparing 4-borono-L-phenylalanine comprises steps of:
    reacting N-protected (S)-4-halophenylalanine of formula (I), a boronating agent and an organolithium to obtain a reaction mixture, wherein the reaction mixture comprises N-protected (S)-4-boronophenylalanine of formula (II) and the R group represents a protecting group;

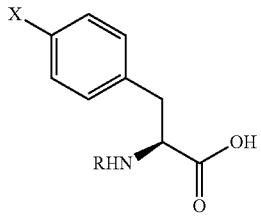

formula (I)

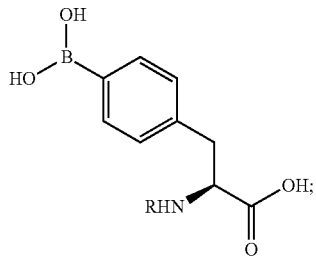

formula (II)

isolating the N-protected (S)-4-boronophenylalanine from the reaction mixture; and
    deprotecting the R group of the N-protected (S)-4-boronophenylalanine to obtain 4-borono-L-phenylalanine (L-BPA).

2. The process according to claim 1, wherein the X group of the N-protected (S)-4-halophenylalanine of formula (I) is iodide or bromide.

3. The process according to claim 1, wherein the R group of the N-protected (S)-4-halophenylalanine of formula (I) and the N-protected (S)-4-boronophenylalanine of formula (II) is selected from the group consisting of: tert-butoxycarbonyl (t-Boc) group, trityl (Trt) group, 3,5-dimethoxyphenylisopropoxycarbonyl(Ddz) group, 2-(4-Biphenyl)isopropoxycarbonyl (Bpoc) group, and 2-nitrophenylsulfenyl (Nps) group.

4. The process according to claim 1, wherein the step of reacting N-protected (S)-4-halophenylalanine, a boronating agent and an organolithium to obtain a reaction mixture comprises reacting the N-protected (S)-4-halophenylalanine, the boronating agent and the organolithium at a temperature ranging from −50° C. to −100° C. to obtain the reaction mixture.

5. The process according to claim 1, wherein an equivalent ratio of the boronating agent to the N-protected (S)-4-halophenylalanine ranges from 2 to 5.

6. The process according to claim 1, wherein an equivalent ratio of the organolithium to the N-protected (S)-4-halophenylalanine is at least 3.

7. The process according to claim 1, wherein the step of reacting N-protected (S)-4-halophenylalanine, a boronating agent and an organolithium to obtain a reaction mixture comprises steps of:
    mixing the N-protected (S)-4-halophenylalanine, a reaction solvent and the boronating agent to obtain a mixed solution; and
    adding an inert organic solvent comprising the organolithium into the mixed solution at a temperature ranging from −50° C. to −100° C., so as to obtain the reaction mixture.

8. The process according to claim 1, wherein the step of isolating the N-protected (S)-4-boronophenylalanine from the reaction mixture comprises steps of:
    adding an aqueous solution to the reaction mixture to obtain a first aqueous layer,
    extracting the first aqueous layer with an extractive solvent to obtain a second aqueous layer, and
    adjusting the pH value of the second aqueous layer to less than 4 to crystallize the N-protected (S)-4-boronophenylalanine, so as to obtain the N-protected (S)-4-boronophenylalanine from the second aqueous layer.

9. The process according to claim 1, wherein the step of deprotecting the R group of the N-protected (S)-4-boronophenylalanine to obtain L-BPA includes a step of acidifying a first organic solvent comprising the N-protected (S)-

4-boronophenylalanine to deprotect the R group of the N-protected (S)-4-boronophenylalanine to obtain L-BPA.

10. The process according to claim 1, wherein the step of deprotecting the R group of the N-protected (S)-4-boronophenylalanine to obtain L-BPA comprises steps of:
   acidifying a first organic solvent comprising the N-protected (S)-4-boronophenylalanine to deprotect the R group of the N-protected (S)-4-boronophenylalanine to obtain an acidic mixture; and
   adjusting the pH of the acidic mixture above 1 to crystallize L-BPA, so as to obtain L-BPA from the acidic mixture.

11. The process according to claim 1, wherein the boronating agent has a $^{10}B$ purity not less than 98%, and the 4-borono-L-phenylalanine is 4-($^{10}B$)borono-L-phenylalanine, and the N-protected (S)-4-boronophenylalanine of formula (II) is N-protected (S)-4-($^{10}B$)boronophenylalanine.

12. The process according to claim 11, wherein the X group of the N-protected (S)-4-halophenylalanine of formula (I) is iodide or bromide.

13. The process according to claim 11, wherein the R group of the N-protected (S)-4-halophenylalanine of formula (I) and the N-protected (S)-4-($^{10}B$)boronophenylalanine of formula (II) is selected from the group consisting of tert-butoxycarbonyl group, trityl group, 3,5-dimethoxyphenylisopropoxycarbonyl group, 2-(4-Biphenyl)isopropoxycarbonyl group, and 2-nitrophenylsulfenyl group.

14. The process according to claim 11, wherein the step of reacting N-protected (S)-4-halophenylalanine, a boronating agent and an organolithium to obtain a reaction mixture comprises reacting the N-protected (S)-4-halophenylalanine, the boronating agent and the organolithium at a temperature ranging from −50° C. to −100° C. to obtain the reaction mixture.

15. The process according to claim 11, wherein an equivalent ratio of the boronating agent to the N-protected (S)-4-halophenylalanine ranges from 2 to 5.

16. The process according to claim 11, wherein an equivalent ratio of the organolithium to the N-protected (S)-4-halophenylalanine is at least 3.

17. The process according to claim 11, wherein the step of reacting N-protected (S)-4-halophenylalanine, a boronating agent, and an organolithium to obtain a reaction mixture comprises steps of:
   mixing the N-protected (S)-4-halophenylalanine, a reaction solvent and the boronating agent to obtain a mixed solution; and
   adding an inert organic solvent comprising the organolithium into the mixed solution at a temperature ranging from −50° C. to −100° C., so as to obtain the reaction mixture.

18. The process according to claim 11, wherein the step of isolating the N-protected (S)-4-($^{10}B$)boronophenylalanine from the reaction mixture comprises steps of:
   adding an aqueous solution to the reaction mixture to obtain a first aqueous layer,
   extracting the first aqueous layer with an extractive solvent to obtain a second aqueous layer, and
   adjusting the pH value of the second aqueous layer to less than 4 to crystallize the N-protected (S)-4-($^{10}B$)boronophenylalanine, so as to obtain N-protected (S)-4-($^{10}B$)boronophenylalanine from the second aqueous layer.

19. The process according to claim 11, wherein the step of deprotecting the R group of N-protected (S)-4-($^{10}B$)boronophenylalanine to obtain 4-($^{10}B$)borono-L-phenylalanine includes a step of acidifying a first organic solvent comprising the N-protected (S)-4-($^{10}B$)boronophenylalanine to deprotect the R group of the N-protected (S)-4-($^{10}B$)boronophenylalanine to obtain 4-($^{10}B$)borono-L-phenylalanine.

20. The process according to claim 11, wherein the step of deprotecting the R group of the N-protected (S)-4-($^{10}B$)boronophenylalanine to obtain 4-($^{10}B$)borono-L-phenylalanine comprises steps of:
   acidifying a first organic solvent comprising the N-protected (S)-4-($^{10}B$)boronophenylalanine to deprotect the R group of the N-protected (S)-4-($^{10}B$)boronophenylalanine to obtain an acidic mixture; and
adjusting the pH of the acidic mixture above 1 to crystallize the 4-($^{10}B$)borono-L-phenylalanine so as to obtain the 4-($^{10}B$)borono-L-phenylalanine from the acidic mixture.

* * * * *